United States Patent [19]

Onken

[11] 4,335,312
[45] Jun. 15, 1982

[54] COUPLING BAR FOR X-RAY TOMOGRAPHY APPARATUS

[75] Inventor: Volker Onken, Hamburg, Fed. Rep. of Germany

[73] Assignee: U.S. Philips Corporation, New York, N.Y.

[21] Appl. No.: 165,176

[22] Filed: Jul. 2, 1980

[30] Foreign Application Priority Data

Jul. 6, 1979 [DE] Fed. Rep. of Germany ....... 2927380

[51] Int. Cl.³ ............................................. G03B 41/16
[52] U.S. Cl. .................................. 250/445 T; 250/523
[58] Field of Search ........................ 250/445 T, 445 R

[56] References Cited

U.S. PATENT DOCUMENTS 3,838,286  9/1974  Prendergast .................... 250/445 T
4,082,955  4/1978  Sell ................................. 250/445 T Primary Examiner—Craig E. Church
Attorney, Agent, or Firm—Marc D. Schechter

[57] ABSTRACT

An X-ray apparatus in which the X-ray source and the image recording device can be detachably interconnected by means of a coupling device. The coupling device includes a coupling rod which slides telescopically in a tube. The coupling device is uncoupled by pressing the supporting arm of the X-ray source downward, thus unblocking a blocking device which connects the coupling rod to the supporting arm. By subsequently raising the supporting arm while latching the blocking device, the coupling rod is left in a storage position. Recoupling of the coupling rod to the arm is effected by releasing the latch of the blocking device and by pressing the supporting arm downward again. It is not necessary to walk around the X-ray apparatus for coupling or uncoupling.

3 Claims, 6 Drawing Figures

COUPLING BAR FOR X-RAY TOMOGRAPHY APPARATUS

BACKGROUND OF THE INVENTION

The invention relates to an X-ray apparatus which includes an X-ray source which is mounted on a horizontal, supporting arm. The X-ray source is movable over a patient table in a horizontal plane. The X-ray apparatus also includes an image recording device which is movable underneath the patient table in a horizontal plane. A coupling device is provided displacing both the X-ray source and the image recording device during tomography.

The coupling device consists of two parts which are telescopically movable with respect to each other and which are rotatable around a horizontal axis. One part is connected to the image recording device while the other part is detachably connected to the supporting arm.

An apparatus of this kind is known as a tomography apparatus of the type LT, made by N. V. Philips' Gloeilampenfabrieken. The coupling device thereof includes a tube, which is pivotably connected to the image recording device, and a coupling rod, which is slidable within the tube and which is detachably connected to the supporting arm. The tube is guided in a sleeve which is rotatable around a horizontal axis which extends perpendicular to the longitudinal direction of the patient table. This horizontal axis defines the sharply imaged tomography plane.

If such an X-ray apparatus is not used for making tomographs but, for example, is used for a so-called Bucky exposure, the coupling rod must be uncoupled from the supporting arm. To this end, it is necessary for the operator to walk around the apparatus and to release a pawl provided on the coupling rod in order to separate the coupling rod from the supporting arm. This requires the use of both hands.

Furthermore, U.S. Pat. No. 3,838,286 discloses an X-ray apparatus with which tomography exposures, angular exposures and so-called Bucky exposures can be made. The coupling device comprises a single rod which remains coupled to the supporting arm during angular exposures and tomography exposures. The coupling rod is slidably guided in the supporting arm for tomography exposures, while for angular exposures the coupling rod is rotatably, but not slidably, connected to the supporting arm. To this end, the coupling rod comprises ribs which are engaged by clamps connected to the supporting arm. When the coupling rod is to be uncoupled from the supporting arm, the operator again must walk around the apparatus, operate two snap mechanisms provided at the lower and the upper extremities of the coupling rod, and lift the rod from the position intended for tomography exposures or angular exposures to a storage position.

SUMMARY OF THE INVENTION

It is an object of the invention to provide an X-ray apparatus of the type described above in which the coupling rod can be uncoupled from the supporting arm is a substantially simplified manner.

To this end, in an X-ray apparatus according to the invention, the coupling rod is detachably connected to the supporting arm at its upper end. A blocking device, mounted on the supporting arm, engages the end of the coupling rod. When the supporting arm is moved downward, the other end of the coupling rod bears against an abutment. As a result, the upper end of the coupling rod is moved upward with respect to the supporting arm. This upward movement disengages the upper end of the rod from the blocking device. Now, by activating a manually operable latch device, the upper end of the rod remains disengaged from the blocking device.

When the blocking device engages the upper end of the coupling rod, the rod is detachably connected to the supporting arm. Uncoupling is performed first by pulling the supporting arm downward, for example by way of the grips provided on the supporting arm for this purpose. The coupling rod is then also moved downward, until it bears against the abutment. As a result, the upper end of the rod is pushed upward relative to the supporting arm, so that the blocking device can be unlocked. When, subsequently, the latch device is activated, the blocking device is retained in the unlocked position. As a result, the supporting arm can now be moved upward, leaving behind coupling rod. The blocking device then remains locked in the latch device. The coupling rod then rests against the abutment.

For coupling, the supporting arm is moved downward again. The blocking device then automatically engages the coupling rod if the latch device is not activated.

According to one embodiment of the invention, the blocking device includes a lever with a blocking pin which fits in a groove. The lever is pivotable against a spring around a pivot. The pivot is situated at one end of the lever on a guide for the coupling rod. The other end of the lever is connected to the latch device by means of a latch pin.

In another embodiment according to the invention, the supporting arm is provided with a sleeve having a conical bore. The upper end of the coupling rod is conically shaped and can be detachably secured in the sleeve's bore by means of two or more wedges. The wedges are pressed apart circumferentially by means of springs. The wedges can be made to engage a lever which forms part of the latch device.

The amount of play between the coupling device and the blocking device is minimum in an X-ray apparatus of this latter kind, even after prolonged use.

BRIEF DESCRIPTION OF THE DRAWING

The invention will now be described in detail with reference to the accompanying drawing figures.

DESCRIPTION OF THE PREFERRED EMBODIMENTS

Figure 1:
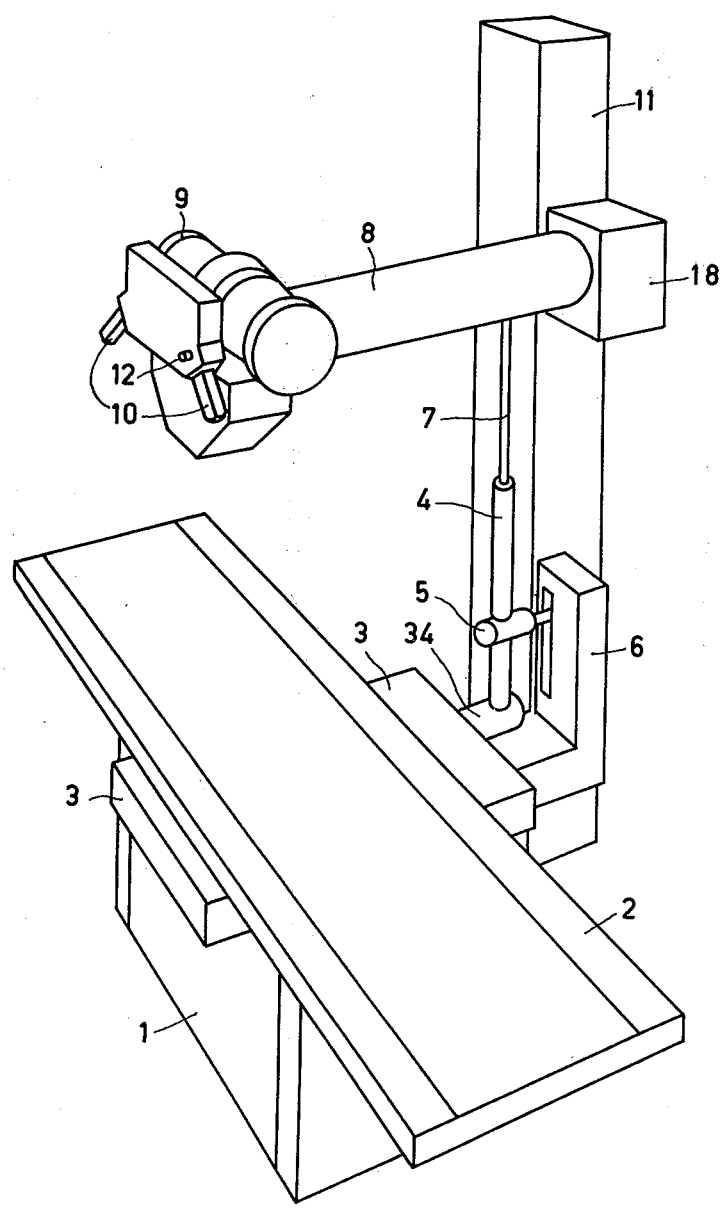
FIG. 1 is a perspective view of an X-ray apparatus according to the invention.

The X-ray apparatus shown in FIG. 1 comprises a horizontally arranged patient table (1, 2). Underneath the patient table there is arranged an image recording device 3 which is movable in a horizontal plane. The image recording device 3 may comprise, for example, a cassette holder for X-ray film cassettes and a scattered radiation grid.

The lower end of a tube 4, having a circular cross-section, is connected to the image recording device 3 at 34. The tube 4 is guided in a sleeve 5 which is rotatable in a vertical tomography column 6 around a horizontal axis which extends perpendicular to the longitudinal direction of the table 2. Because the sleeve 5 is displaceable in the vertical direction within the tomography column 6, the position of the layer which is sharply imaged during the exposure can be adjusted.

A around coupling rod 7, which is telescopically displaceable in the tube 4, is connected to a tubular supporting arm 8. In conjunction with the tube 4, this rod 7 forms a coupling device between the image recording device 3 and the supporting arm 8, or an X-ray source 9 connected thereto. The supporting arm 8, which extends horizontally and perpendicular to the longitudinal direction of the table 2, is secured in a carriage 18 so as to be rotatable around its longitudinal axis. The carriage 18 is displaceable in the vertical direction along a vertical column 11. The column 11 is displaceable in a direction parallel to the longitudinal direction of the table.

The coupling rod 7 may be coupled to and uncoupled from the supporting arm 8 when the column 11 is in a position in which the X-ray source 9 is directly above the image recording device 3. As will be described below with reference to FIGS. 2 and 3, uncoupling is performed by pulling the supporting arm 8, or the X-ray source 9 connected thereto, downwards by means of the grips 10. This is continued until the lower end of the coupling rod 7 (rod 7 being longer than the tube 4) abuts against an abutment 60 which may be formed by a horizontal face in the tomography column 6. Now, the operator operates a latch device (22, 25) by means of a button 12 provided on the X-ray source 11. When the X-ray source 9 is subsequently raised again, the coupling rod 7 is uncoupled from arm 8. Now, by pressing the supporting arm 8 downwards so that the coupling rod 7 again engages a blocking device (15, 31, or 35), yet to be described, the coupling is reestablished.

Figure 2:
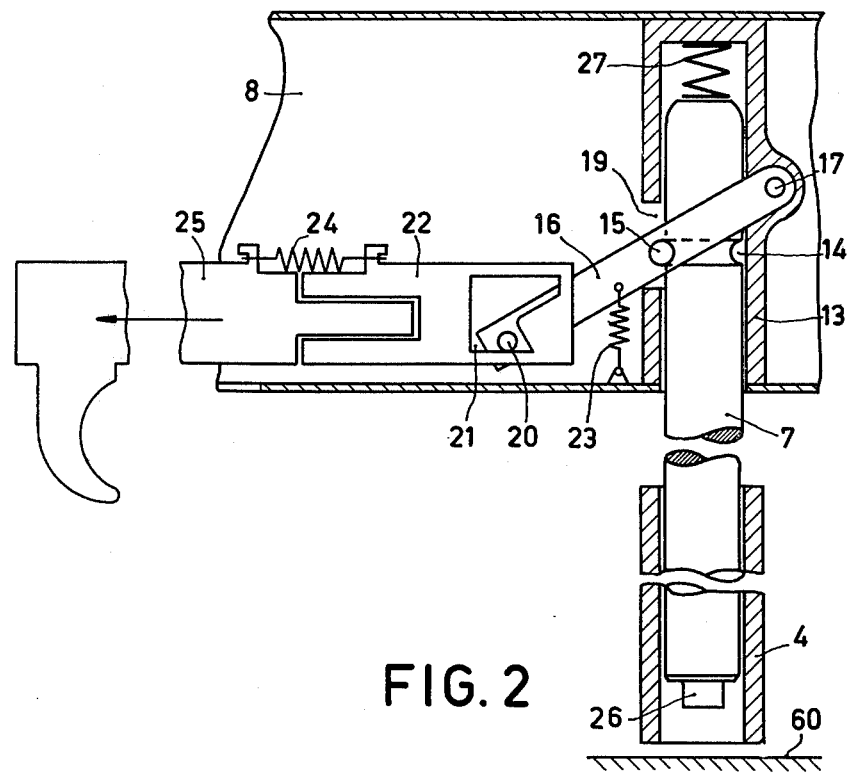
FIG. 2 is a cross-sectional view of a part of the supporting arm and the coupling device in the blocked condition.

As appears from FIG. 2, the tubular supporting arm 8 includes a tubular guide 13 which extends perpendicular to the longitudinal direction of the supporting arm 8. Guide 13 accommodates the coupling rod 7. Near its upper end, the coupling rod 7 has an annular groove 14 which can be engaged by a blocking pin 15 via an opening 19 in the guide 13.

The blocking pin 15 is connected to a lever 16 which is pivotable at one end around a pivot 17 provided on the guide 13. At its other end, the lever 16 includes a latch pin 20 which is guided in a recess 21 of a latch device (22, 25). The latter end is pulled downwards by a spring 23 which is connected to the supporting arm 8.

The portion 22 of the latch device (22, 25) is connected, via a spring 24, to a system of rods 25. This rod system is only partly shown for the sake of simplicity. Rods 25 extend through the supporting arm 8 to the vicinity of the X-ray source 9 in the front of the X-ray apparatus. As a result, that the latch device (22, 25) can be operated from the front of the apparatus by keeping the spring 24 under tension. It will be clear that this can be accomplished fully mechanically, by means of levers coupled to the system of rods. However, the system of rods is preferably operated by means of an electromagnet which is actuated by means of a button 12 (see FIG. 1).

On the lower end of the coupling rod 7 guided in the tube 4 there is provided a rubber absorber 26. Underneath the tube 4 there is provided a horizontal face 60 which serves as an abutment for the coupling rod 7. With the coupling rod 7 in the position shown in FIG. 2, a spring 27 is compressed between the top of rod 7 and guide 13. The spring 27 exerts a downward force on the coupling rod 7.

Figure 3:
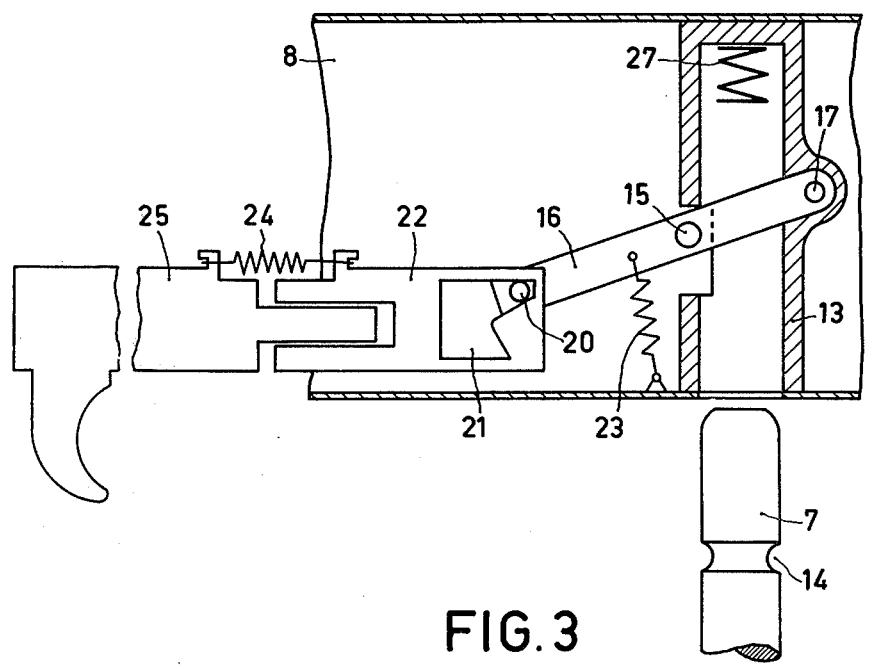
FIG. 3 is a cross-sectional view of a part of the supporting arm and the coupling device in the unblocked condition.

For uncoupling the coupling rod 7, the operator actuates the electromagnet (not shown for the sake of simplicity) by depressing the button 12. The system of rods 25, connected to the armature of the electromagnet, is then displaced in the direction of the arrow (see FIG. 2), so that the spring 24 is tensioned and the latch pin 20 is displaced fully to the right in the recess 21 of the latch device portion 22. When the operator subsequently moves the supporting arm 8 downwards, by means of the grips 10 (FIG. 1), until the absorber 26 of the coupling rod 7 bears against the abutment 60, the coupling rod 7 is diplaced against the force of the spring 27 with respect to the guide 13. The free left end of the lever 16 is then pivoted upwards, until the blocking pin 15 completely disengages from the groove 14. As a result of this movement of the lever 16, the latch pin 20 moves upwards in the recess 21 of the latch device portion 22 and is retained in the right upper position because the latch device portion 22 is pulled in the direction of the arrow by the spring 24 (FIG. 3). When the supporting arm 8 or the X-ray source 9 is subsequently raised, in this situation, the coupling rod 7 remains behind with respect to the supporting arm 8 and guide 13. The blocking pin 15 does not engage the groove 14 because the latch pin 20 is retained in the upper position.

When the coupling rod 7 is to be reconnected to the supporting arm 8, the supporting arm 8 is moved downward. The guide 13 is then placed over the upper end of the coupling rod 7 until the blocking pin 15 contacts the coupling rod 7. The coupling rod 7 subsequently presses the blocking pin 15 outwards and slides further into the guide 13 until the groove 14 is situated at the area of the blocking pin 15. At this position the blocking pin 15 is blocked by the groove 14. The latch device portion 22 is again in the position shown in FIG. 2 because the electromagnet has been deactivated by depressing the button 12 a second time.

Figure 4:
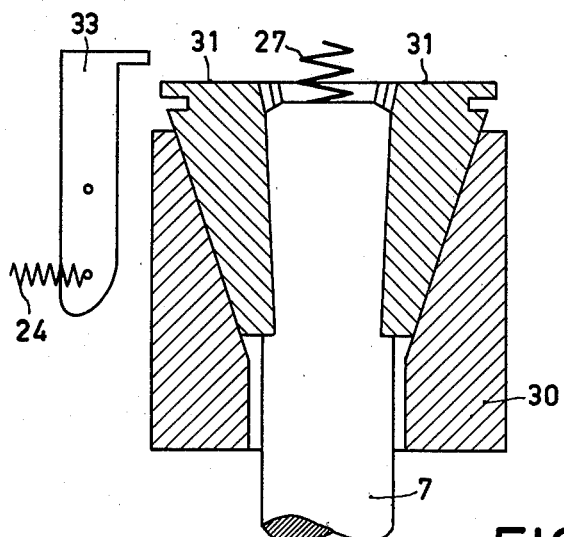
FIG. 4 is a cross-sectional view of a further embodiment of the blocking device according to the invention.
Figure 5:
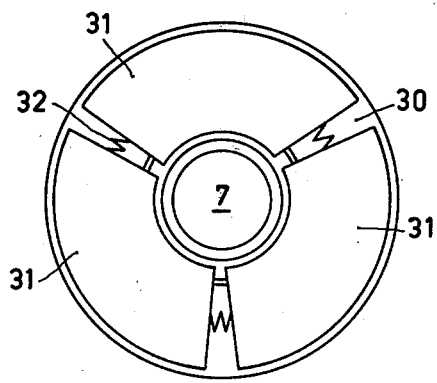
FIG. 5 is a plan view of the blocking device of FIG. 4.

In the embodiment shown in the FIGS. 2 and 3, frequent use could cause such lateral play between the coupling rod 7 and the guide 13 that unsharp images could be produced in some cases. FIGS. 4 and 5 illustrate an embodiment of the invention in which there is no lateral play between the coupling rod 7 and its guide 13, not even after frequent use. The parts of the apparatus which correspond to FIGS. 1 to 3 have been omitted for the sake of simplicity in FIGS. 4 and 5.

FIG. 4 shows a cylindrical sleeve 30 which is connected to the supporting arm 8 in a manner not shown. The cylindrical sleeve 30 has a partly conical bore which widens in the upwards direction. The smallest diameter of the bore in the sleeve 30 is substantially larger than the largest diameter of the coupling rod 7.

The coupling rod 7 has a shoulder near its upper end. The part of the coupling rod 7 which is situated above this shoulder also has a conical shape. However, the conical shape is less pronounced than that of the sleeve 30.

The blocking device is now formed by three wedges 31 which are regularly spaced with respect to each other around the circumference of rod 7. The angle of the wedges 31 equals the angle between the sleeve 30 and the coupling rod 7. Between the wedges 31, there are provided springs 32 (see FIG. 5) which force the wedges apart. Springs which exert a downwardly directed forces on the upper end faces of the wedges 31 may also be provided.

As appears from FIG. 4, the upper end of the coupling rod 7 is clamped by the wedges 31 when a downwardly directed force (for example, the weight of the coupling rod plus the force of the spring 27) is exerted on the coupling rod 7. Instead of three wedges two, four or more wedges can also be used. Such clamping of the coupling rod 7 lessens the amount of lateral play.

The blocking device (clamps 31) in the embodiment shown in FIGS. 4 and 5 may be unblocked by pressing supporting arm 8 downwards, together with the sleeve 30, until the lower end of the coupling rod 7 abuts against an abutment. As a result, an upwardly directed force is exerted on the coupling rod 7 which pushes the wedges 31 out of the sleeve 30. When the wedges are subsequently locked in the upper position, for example, by means of a lever 33 which is to be operated by the operator via a system of rods (not shown) and a spring 24, the coupling rod 7 can be readily uncoupled by moving the supporting arm 8 upward. The upper end of the coupling rod 7 then disengages from the wedges 31.

FIG. 4 shows only a single lever 33 for the sake of simplicity. All levers have been omitted in FIG. 5. However, each wedge 31 requires one lever 33. Instead of using a lever, an annular electromagnet could be provided above the upper end face of the wedges 31. When this magnet is energized, wedges 31 are locked in an upper position. When the electromagnet is not energized, the wedges 31 can be pressed downwards by an annular spring which is arranged inside or outside the annular electromagnet and which bears against the upper end face of the wedges 31.

The coupling rod of the device shown in FIGS. 4 and 5 can be coupled in the same way as in the device shown in the FIGS. 2 and 3. The supporting arm is pressed downward so that the upper end of the coupling rod pushes the wedges 31 upward. When the inner diameter of the blocking device, formed by the wedges 31 is so large that the coupling rod fits therein the rod 7 slides into the blocking device until the lower end faces of the wedges 31 bear against the shoulder of the coupling rod. When the supporting arm is subsequently moved upwards again, the spring 27 and the weight of the coupling rod 7 produce a downwardly directed force, so that the coupling rod 7 becomes clamped to sleeve 30.

Figure 6:
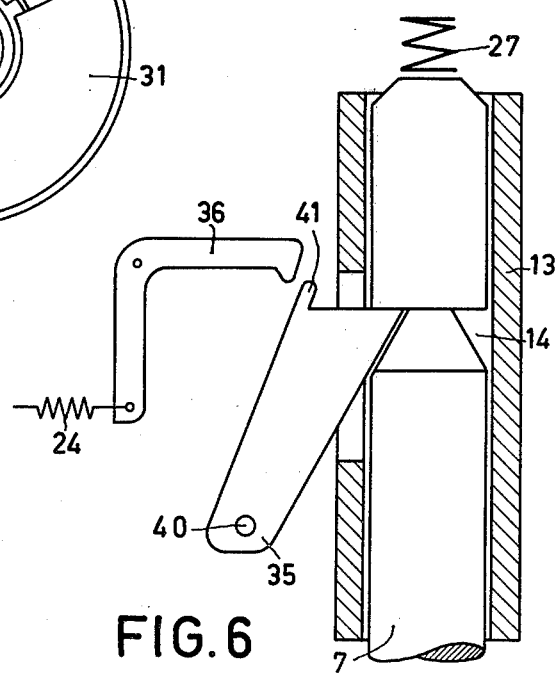
FIG. 6 is a cross-sectional view of another embodiment of the blocking device according to the invention.

In the embodiment shown in FIG. 6, parts of the apparatus which correspond to parts shown in FIGS. 1 to 3 have been omitted for the sake of simplicity. A guide 13, in which the coupling rod 7 is slideably disposed, is again connected to the supporting arm. The groove 14 near the upper end of the coupling rod 7 is formed by a local, gradual decrease of the diameter of the coupling rod 7 which terminates at a shoulder which extends transverse to the longitudinal direction of the coupling rod 7. Above the shoulder, the coupling rod 7 has the same diameter as below the groove. The groove 14 thus formed engages a lever 35 which is pivotable around a shaft 40 which is rigidly connected to the supporting arm and is shaped so that it suitably engages groove 14 (see FIG. 6).

When a downwardly directed force (the force of gravity and the force of a spring 27) is exerted on the coupling rod 7, the lever 35 supports the coupling rod 7. When the supporting arm is pressed downward, the coupling rod 7 slides upward in the guide 13. The lever 35 is then pivoted and disengaged from the groove 14. The lever 35 has a cam 41 which is engaged by another lever 36 provided on the supporting arm. Lever 36 is made to engage cam 41 by means of a system of rods or by energizing an electromagnet, the system of rods or electromagnet pulling a spring 24, connected to the lever 36, to the left in the manner already described with reference to FIGS. 1 to 3.

When the right end of the lever 36 engages the cam 41, thus retaining the cam, the coupling rod 7 can be released from the guide 13 by moving the supporting arm upward. The coupling rod may be recoupled to the arm by first releasing the spring 24 so that the cam 41 is no longer engaged by the lever 36. Lever 35 then pivots to the right. When the supporting arm is then pressed downward, the coupling rod 7 moves upward in the guide 13 and the the lever 35 engages groove 14.

The described embodiments all have a common feature in that the coupling rod 7 can be uncoupled from the supporting arm 8 only if the arm is pressed downwards (in a position which is situated below the customary position of the supporting arm for tomography) and if the latch device which unblocks the blocking device is operated (by means of the button 12, FIG. 1). Accidental uncoupling of the coupling rod 7 by the simple pressing of the button 12 by the operator (i.e. when the arm 8 is not in the lowered position) is thus not possible.

In all described embodiments of the invention, the uncoupled coupling rod 7 is stored on the abutment 60. The supporting arm 8 can be moved downward, for coupling or uncoupling, from the free side of the apparatus; it is not necessary for the operator to move to the side of the apparatus where the coupling rod is situated.

What is claimed is:

1. An X-ray examination apparatus comprising:
    a patient table;
    a supporting arm, extending in a horizontal direction, movable over the patient table in a plane which extends in a horizontal direction;
    an X-ray source mounted on the supporting arm;
    an image recording device movable underneath the patient table in a plane which extends in a horizontal direction; and
    a coupling device having two parts, one part being connected to the image recording device and the other part being detachably connected to the supporting arm, said coupling device being rotatable around a horizontal axis, said two parts being telescopically movable with respect to each other;
    characterized in that:
    the coupling device comprises a coupling rod having a first end and a second end, said first end being detachably connected to the supporting arm; and
    the apparatus further comprises:
    a blocking device, mounted on the supporting arm, for engaging the first end of the coupling rod, said blocking device disengaging the first end of the coupling rod whenever the first end moves upward with respect thereto;

an abutment, positioned so that when the supporting arm and coupling rod connected thereto are moved downward, the second end of the coupling rod bears on the abutment so that the first end of the coupling rod moves upward with respect to the supporting arm; and a manually operable latch device for maintaining the blocking device in a disengaged state after the blocking device is disengaged from the first end of the coupling rod.

2. An X-ray examination apparatus as claimed in claim 1, characterized in that:

the first end of the coupling rod is provided with a groove;

the supporting arm is provided with a guide in which the first end of the coupling rod may be slidably arranged;

the blocking device comprises a lever having one end pivotably connected to the guide, said lever comprising a blocking pin which fits into the groove, said lever being spring biased to push the blocking pin toward the coupling rod; and the latch device is connected to the lever by means of a latch pin connected to another end of the lever.

3. An X-ray examination apparatus as claimed in claim 1, characterized in that:

the first end of the coupling rod is conically shaped, the diameter of the end of the rod decreasing in the downward direction;

the supporting arm is provided with a sleeve having a conical bore in which the first end of the coupling rod may be slidably arranged;

the blocking device comprises two or more wedges, said wedges being spring biased to remain circumferentially spaced in the conical bore; and the latch device comprises a lever for engaging the wedges.

* * * * *